United States Patent [19]

Marshall et al.

[11] Patent Number: 5,487,748
[45] Date of Patent: Jan. 30, 1996

[54] BLOOD SAMPLING DEVICE

[75] Inventors: Jeremy Marshall; David D. Crossman, both of Oxford, United Kingdom

[73] Assignee: Owen Mumford Limited, Oxford, United Kingdom

[21] Appl. No.: 307,624
[22] PCT Filed: Mar. 30, 1993
[86] PCT No.: PCT/GB93/00650
  § 371 Date: Sep. 27, 1994
  § 102(e) Date: Sep. 27, 1994
[87] PCT Pub. No.: WO93/19671
  PCT Pub. Date: Oct. 14, 1993

[30] Foreign Application Priority Data

Apr. 1, 1992 [GB] United Kingdom ............... 9207120

[51] Int. Cl.⁶ ............................................ A61B 5/14
[52] U.S. Cl. ..................... 606/182; 606/181; 128/770
[58] Field of Search ................. 128/749, 751, 128/753, 754, 760, 770; 609/263; 606/181, 182

[56] References Cited

U.S. PATENT DOCUMENTS

| | | | |
|---|---|---|---|
| 4,375,815 | 3/1983 | Burns | 606/182 |
| 4,539,988 | 9/1985 | Shirley et al. | |
| 4,577,630 | 3/1986 | Nitzche et al. | 606/182 |
| 4,976,724 | 12/1990 | Nieto et al. | 606/181 |
| 5,100,427 | 3/1992 | Crossman et al. | 606/182 |
| 5,282,822 | 2/1994 | Macors et al. | 606/181 X |
| 5,304,193 | 4/1994 | Zhadonov | 128/770 X |
| 5,368,047 | 11/1994 | Suzuki et al. | 128/770 X |

FOREIGN PATENT DOCUMENTS

| | | |
|---|---|---|
| 0255338 | 2/1988 | European Pat. Off. |
| 0427406 | 5/1991 | European Pat. Off. |
| 0433050 | 6/1991 | European Pat. Off. |
| 0458451 | 11/1991 | European Pat. Off. |
| 771890 | 10/1934 | France. |
| 4213351 | 10/1993 | Germany ............... 128/770 |

*Primary Examiner*—Sam Rimell
*Attorney, Agent, or Firm*—Young & Thompson

[57] ABSTRACT

A blood sampling device has a tubular body (1, 2) housing a spring loaded (7) lancet (8) whose needle (17) is initially protected by a cap (20) which projects out from the forward end of the body. A rocker-like trigger (9) is formed as part of the moulded body (1,2) and holds the lancet (8) in a retracted position when the lancet is pushed back by the projecting cap (20). The cap can then be removed by a twist and pull action, breaking it free from the lancet body, which is prevented from rotating. Pressure on the trigger (9) releases the lancet (8), which is shot forward by the spring (7) for momentary projection of the needle tip (19), and then retracts to bring the needle tip within the body.

7 Claims, 1 Drawing Sheet

BLOOD SAMPLING DEVICE

This invention relates to blood sampling devices, and in particular to a pricker to draw a small drop of blood for analysis. Such prickers are widely used by diabetics, for example, who need to know their sugar level. However, there are many other applications.

These days, with AIDS, there is widespread concern surrounding the use of needles and their part in transmitting disease. Once a needle has been used on an infected person, subsequent use or an accidental prick on another could be fatal.

There is therefore a growing demand for a pricker which can be used just once and, having been used, is automatically rendered safe for carriage and disposal.

Several such prickers have been proposed, for example in EP-A-0427406 and EP-A-0433050. These work well, and use a lancet which has been in production for many years. However, it is important for disposable objects with a very transient life to be made as simply and cheaply as possible, without compromising on effectiveness. This the present invention aims to do.

According to the present invention there is provided a disposable pricker comprising an elongate body with a spring-loaded lancet carried therein, the lancet tip normally being within the body, a trigger mechanism to retain the lance in a fully retracted position energising the spring means and actuable to release the lancet to cause the tip to have a momentary position projecting from the forward end of the body, and an elongate cap encasing the lancet tip and having a head external of the body, the cap providing means to retract the lancet and being breakable free of the lancet to leave the tip exposed.

Conveniently, the trigger mechanism comprises a rocker with an outwardly projecting portion for manual operation and an inwardly projecting portion for co-operation with the lancet. The rocker may be centrally connected to the main part of the body by small webs which are distortable to allow the rocker action.

It has been found beneficial for the rocker to have further means connecting it to the body to resist pivoting below a predetermined actuating force. This prevents accidental operation.

Preferably the trigger mechanism is formed integrally with the body, which will generally be moulded in plastics material with a certain resilience. As the lancet is pushed back to prime the device, a projection on it can snap past an inwardly projecting lug on one end of the trigger and this will temporarily hold the lancet retracted. Pressure on the other end of the trigger will raise the lug clear and release the lancet.

Although the body and trigger will preferably be integral, they may initially be moulded as two main parts, one of which contains the trigger, connected by a thin flexible web, presenting the body in an opened out condition. When the lancet and spring means are in place, these two parts will be folded together and secured, as by adhesive or ultrasonic welding.

In order to assist in breaking the cap away from the lancet, the latter may have an engagement with the interior of the body that prevents it rotating about its longitudinal axis, at least when the lancet is retracted. The cap may therefore be twisted off by one hand with the other holding the body.

Another characteristic of the fit of the lancet within the body is preferably that, once the lancet has been fired, it should tend to lie skew to the axis of the body. This would make it difficult, using the twisted off cap for example, to insert it again and press the lancet back for possible re-use.

For a better understanding of the invention, one embodiment will now be described, by way of example, with reference to the accompanying drawing, in which.

Figure 1:
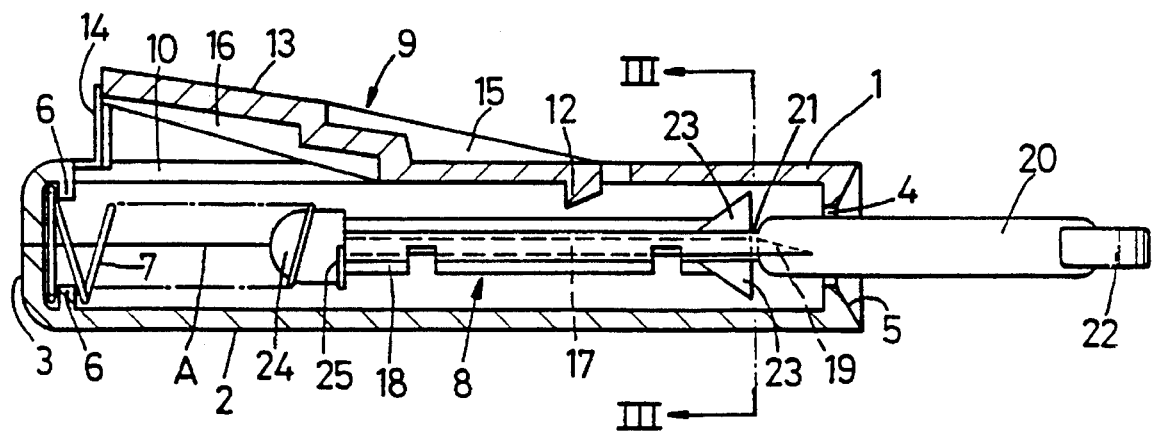
FIG. 1 is a longitudinal section of a blood sampling pricker.

The body of the pricker is of generally square tubular form and is of moulded plastics construction. Two channel-like parts 1 and 2 are closed together and secured in a plane A to form the tube, which is closed at the rear end 3 and which has an opening 4 at the forward end. An external bevel 5 around this opening forms a shallow recess into which a thumb or finger, for example, can be pressed for pricking.

The parts 1 and 2 have interior lugs 6 opposing each other close to the rear end 3 to provide a trap for one end of a coil spring 7 by which a lancet 8, to be described in more detail below, is made captive. Otherwise, the lower part 2 is plain. However, the upper part 1 has a trigger 9 integrally moulded with it. The trigger lies largely within a bottle shaped aperture 10, the head of the bottle pointing forwards, and in plan view the trigger 9 is similarly shaped but smaller. Its main connection to the part 1 is by short bridges or webs 11 at the shoulders of the "bottle" and in the normal, relaxed state, the pricker adopts the position shown in FIG. 1. In that case, the forward end of the trigger, in front of the webs 11, is generally flush with the interior of the upper part of the body 1, but at its leading end a hook 12 projects down into the body cavity. The hook 12 has a shallow slope facing forwards and a steep rear face. To the rear of the webs 11, the pricker 9 steps upwardly to a thumb pad 13 by which it can be pivoted, and there are two optional thin L-shaped strips 14 connecting the rear corners of this pad 13 to the main part 1 of the body. When the pad 13 is pressed, these strips 14 (if provided) buckle or shear off at their connection to the rear end 3 and the trigger pivots to move the hook 12 out clear of the interior of the body 1. Longitudinal reinforcing ribs 15 and 16 make the trigger 9 an effectively rigid rocker.

Figure 2:
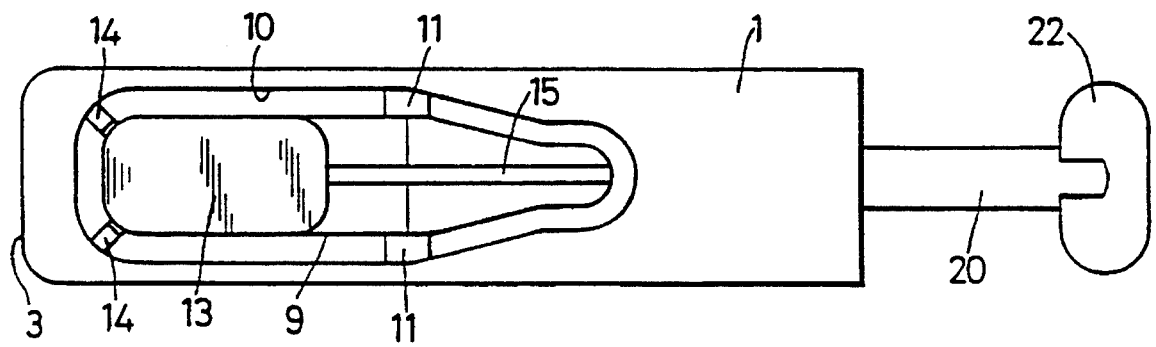
FIG. 2 is a plan view of the pricker of FIG. 1.

The strips 14 are not necessary if the device is to be provided with the lancet 8 as shown in FIGS. 1 and 2 and as described below, when it has to be cocked by the user before release. But there is also a call for pre-cocked devices and then there is a need to prevent premature actuation of the trigger, as by careless handling for example. The strips 14 perform this safety function, since they demand a very positive pressure on the pad 13. They will generally buckle or shear suddenly, giving a quick action of the trigger and clean release of the lancet. A pre-cocked lancet will still usually have a cap, as described below, to maintain sterility of the needle.

The lancet 8 comprises a steel needle 17 almost entirely encased in a cruciform-section jacket 18, except for its tip 19. Initially, this tip is concealed within the rear end of an elongated cap 20 joined to the jacket 18 by a weak collar 21. The cap 20 passes freely through the aperture 4 and terminates outside the body 1 in a tab 22.

Figure 3:
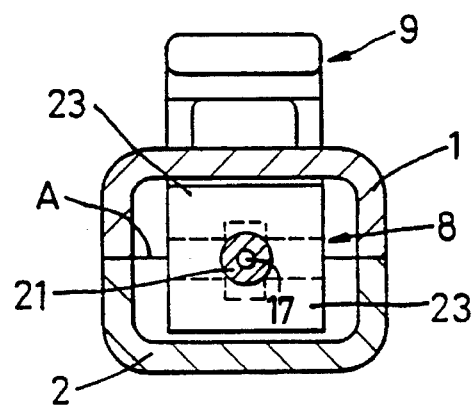
FIG. 3 is a cross-section on the line III—III of FIG. 1.

Just to the rear of the collar 21, the jacket 18 terminates at its forward end in two opposed wedges 23, their sloping sides facing rearwardly and being convergent, while their forward sides are co-planar and at right angles to the axis of the needle 17. Viewed end-on, as in FIG. 3, the wedges 23 form a rectangle slightly smaller than the inner cross-sectional profile of the body 1,2. At the rear end, the jacket is formed with a domed stud 24 with an undercut slot 25 to locate and trap the forward end of the coil spring 6, which fits over the stud 24.

Initially, the pricker is as shown in FIG. 1, with the cap 20 projecting well beyond the forward end of the body 1, 2 but with the tip 19 of the needle still inside the body and encased by the rear end of the cap 20. To prime or cock the trigger, the cap is simply pressed axially towards the body 1 causing the lancet to compress the spring 7. As one of the wedges 23 reaches the hook 12, the sloping surfaces cooperate to rock the trigger 9 until the wedge 23 snaps pas the hook 12, whereupon the resilience of the webs 11 and the strips 14 restores the trigger back to the FIG. 1 position to trap the lancet in a fully retracted position. The tab 22 is then grasped and, with the body 1 held, is given a twist. The wedges 23 prevent the lancet rotating within the body 1, and so the weak collar 21 is sheared. The cap 20 can then be withdrawn. A thumb or finger is pressed into the aperture 4 and the pad 13 is pressed releasing the lancet. It shoots forward to make the prick and, the spring 7 momentarily having been over extended, draws the lancet back a little so that the tip 19 ends up safely inside the body 1,2.

Although the leading end of the lancet does not have much freedom of movement within the body 1,2 its rear end can shift up and down. The lancet will therefore tend to come o rest slightly skew to the axis of the body 1,2. Certainly, if an attempt is made to retract the lancet again by inserting something through the hole 4, the spring 7 and the lancet will tend to go out of alignment. This makes it very difficult to use the discarded cap to poke the lancet back for possible re-use. Thus, the pricker and cap will have to be discarded.

We claim:

1. A disposable pricker comprising an elongate body with a lancet non-rotatably carried therein, the lancet tip normally being within the body, a spring urging the lancet in a direction to project its tip from the body, a trigger mechanism carried by the body with a portion within the body arranged to retain the lancet in a fully retracted position energizing the spring and a second portion outside the body manually actuable to release the lancet to cause the tip to have a momentary position projecting from an opening in the forward end of the body, and a cap encasing the lancet tip and having a shank traversing said opening, wherein said shank extends outwardly of said body through said opening a distance sufficient to permit said lancet to be moved against the action of said spring to said fully retracted position solely by pushing said cap further into said body through said opening, and wherein said cap is breakable free of the lancet by twisting when so retracted to leave the tip exposed within said body.

2. A disposable pricker as claimed in claim 1, characterised in that the body is moulded in two parts connected by a thin flexible web, presenting the body in an opened out condition but closeable together when the lancet and spring means are in place.

3. A disposable pricker as claimed in claim 1, characterised in that the trigger mechanism comprises a rocker and is formed integrally with the body, said trigger and said body being formed of moulded plastics material.

4. A disposable pricker as claimed in claim 3, characterised in that the rocker is centrally connected to the body by first webs which are distortable to allow the rocker action.

5. A disposable pricker as claimed in claim 4, characterised in that the rocker has second webs connecting it to the body to resist pivoting below a predetermined actuating force but once that force has been exceeded to offer little further resistance.

6. A disposable pricker as claimed in claim 1, characterised in that the lancet has a detent and the first portion of the trigger mechanism is a lug that co-operates with the detent, the detent being arranged to snap past the lug as the lancet is retracted to hold the lancet in that position.

7. A disposable pricker as claimed in claim 1, characterised in that the lancet is substantially narrower than the body so that, once the lancet has been fired, it will lie skew to the axis of the body.

* * * * *

REEXAMINATION CERTIFICATE (3494th)

United States Patent [19]

Marshall et al.

[11] B1 5,487,748

[45] Certificate Issued  Apr. 14, 1998

[54] BLOOD SAMPLING DEVICE

[75] Inventors: Jeremy Marshall; David D. Crossman, both of Oxford, United Kingdom

[73] Assignee: Owen Mumford Limited, Oxford, United Kingdom

Reexamination Request:
No. 90/004,365, Sep. 11, 1996

Reexamination Certificate for:
Patent No.: 5,487,748
Issued: Jan. 30, 1996
Appl. No.: 307,624
Filed: Sep. 27, 1994

[22] PCT Filed: Mar. 30, 1993

[86] PCT No.: PCT/GB93/00650

§ 371 Date: Sep. 27, 1994

§ 102(e) Date: Sep. 27, 1994

[87] PCT Pub. No.: WO93/19671

PCT Pub. Date: Oct. 14, 1993

[30] Foreign Application Priority Data

Apr. 1, 1992 [GB] United Kingdom ............... 9207120

[51] Int. Cl.$^6$ .................................................. A61B 5/14
[52] U.S. Cl. .......................... 606/182; 606/181; 128/770
[58] Field of Search .................................. 118/749, 751, 118/753, 754, 760, 770; 606/181, 182

[56] References Cited

U.S. PATENT DOCUMENTS 5,147,375  9/1992  Sullivan et al. .

*Primary Examiner*—Sam Rimell

[57] ABSTRACT

A blood sampling device has a tubular body (1, 2) housing a spring loaded (7) lancet (8) whose needle (17) is initially protected by a cap (20) which projects out from the forward end of the body. A rocker-like trigger (9) is formed as part of the moulded body (1,2) and holds the lancet (8) in a retracted position when the lancet is pushed back by the projecting cap (20). The cap can then be removed by a twist and pull action, breaking it free from the lancet body, which is prevented from rotating. Pressure on the trigger (9) releases the lancet (8), which is shot forward by the spring (7) for momentary projection of the needle tip (19), and then retracts to bring the needle tip within the body.

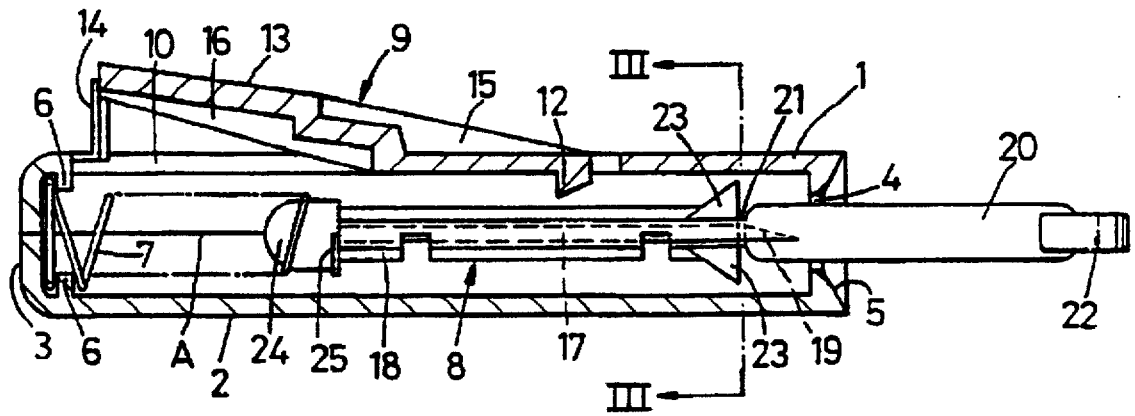

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–7 is confirmed.

New claims 8–9 are added and determined to be patentable.

*8. A disposable pricker comprising an elongate body with a lancet non-rotatably carried therein, the lancet tip normally being within the body, a spring urging the lancet in a direction to project its tip from the body, a trigger mechanism carried by the body with a portion within the body arranged to retain the lancet in a fully retracted position energizing the spring and a second portion outside the body manually actuable to release the lancet to cause the tip to have a momentary position projecting from an opening in the forward end of the body, and a cap encasing the lancet tip and having a shank traversing said opening, wherein said shank extends outwardly of said body through said opening a distance sufficient to permit said lancet to be moved against the action of said spring to said fully retracted position solely by pushing said cap further into said body through said opening, wherein said cap is breakable free of the lancet by twisting when so retracted to leave the tip exposed within said body, said cap having lateral ears at one end of said shank remote from said body, to permit grasping of said cap and twisting thereof to break said cap free of the lancet.*

*9. A disposable pricker comprising an elongate body with a lancet non-rotatably carried therein, the lancet tip normally being within the body, a spring urging the lancet in a direction to project its tip from the body, a trigger mechanism carried by the body with a portion within the body arranged to retain the lancet in a fully retracted position energizing the spring and a second portion outside the body manually actuable to release the lancet to cause the tip to have a momentary position projecting from an opening in the forward end of the body, and a cap encasing the lancet tip and having a shank traversing said opening, wherein said shank extends outwardly of said body through said opening a distance sufficient to permit said lancet to be moved against the action of said spring to said fully retracted position solely by pushing said cap further into said body through said opening, wherein said cap is breakable free of the lancet by twisting when so retracted to leave the tip exposed within said body, wherein said lancet comprises a jacket encasing a steel needle except for a tip portion thereof, and wherein said cap is formed integrally with said jacket and joined thereto by a weak collar portion, such that twisting of said cap shears the weak collar, thereby to break said cap free of the lancet.*

* * * * *